United States Patent
Madaus et al.

(10) Patent No.: US 6,626,176 B1
(45) Date of Patent: Sep. 30, 2003

(54) METHOD AND DEVICE FOR SWITCHING THE INSPIRATION OR EXPIRATION PHASE DURING CPAP THERAPY

(75) Inventors: Stefan Madaus, Krailing (DE); Harald Vögele, Gauting (DE); Jutta Griebel, Igensdorf (DE)

(73) Assignee: MAP Medizintechnik fur Arzt und Patient GmbH & Co. KG (DE)

( * ) Notice: Subject to any disclaimer, the term of this patent is extended or adjusted under 35 U.S.C. 154(b) by 0 days.

(21) Appl. No.: 09/763,295

(22) PCT Filed: Aug. 19, 1999

(86) PCT No.: PCT/EP99/06080

§ 371 (c)(1),
(2), (4) Date: Apr. 12, 2001

(87) PCT Pub. No.: WO00/10633

PCT Pub. Date: Mar. 2, 2000

(30) Foreign Application Priority Data

Aug. 19, 1998 (DE) .......................... 198 37 656
Oct. 8, 1999 (DE) .......................... 198 46 462

(51) Int. Cl.[7] .......................... A61M 16/00; A62B 7/00; F16K 31/02
(52) U.S. Cl. .......................... 128/204.23; 128/204.21; 128/204.22; 128/204.18
(58) Field of Search .......................... 128/209.18, 204.21, 128/204.22, 204.23

(56) References Cited

U.S. PATENT DOCUMENTS 4,676,232 A * 6/1987 Olsson et al. .................. 601/41
4,686,974 A * 8/1987 Sato et al. ............. 128/204.23
5,377,671 A * 1/1995 Biondi et al. .......... 128/204.23
5,740,797 A * 4/1998 Dickson ................. 128/204.28

FOREIGN PATENT DOCUMENTS

| EP | 606 687 A2 | 7/1994 | .......... A61M/16/00 |
| EP | 656 216 A2 | 6/1995 | .......... A61M/16/00 |
| EP | 714 670 A2 | 6/1996 | .......... A61M/16/00 |
| EP | 722 747 A2 | 7/1996 | .......... A61M/16/00 |
| WO | WO 93/08857 | 5/1993 | .......... A61M/16/00 |
| WO | WO 98/35715 | 8/1998 | .......... A61M/16/00 |

OTHER PUBLICATIONS

IEEE Transactions on Biomedical Engineering, vol. BME–34, No. 6, pp 437–443, Jun. 1987.
Int. J. Control, vol. 56, No. 5, pp 1039–1057, 1992.
Computers and Biomedical Research2, pp 411–429, 1969.
IEEE Transactions on Biomedical Engineering, vol. BME–19, No. 1, pp 47–53, Jan. 1972.
International Search Report for PCT/EP99/ 06080t.

* cited by examiner

Primary Examiner—Weilun Lo
Assistant Examiner—Darwin P. Erezo
(74) Attorney, Agent, or Firm—Ohlandt, Greeley, Ruggiero & Perle, LLP; George W. Rauchfuss, Jr.

(57) ABSTRACT

A method and a device for switching to the inspiration or expiration phase during CPAP therapy are disclosed. By means of a first high threshold value and a second low threshold value non-specific influences on the first derivative of the gas flow curve are suppressed in the corresponding breathing phase and the transition to the corresponding following gas phase is determined with high sensitivity. The invention further relates to methods for recognizing and suppressing the influence of the pulse or for switching to the inspiration phase in case of shallow breathing. The advantages of the invention are greater switching accuracy and improved safety for the patient.

19 Claims, 4 Drawing Sheets

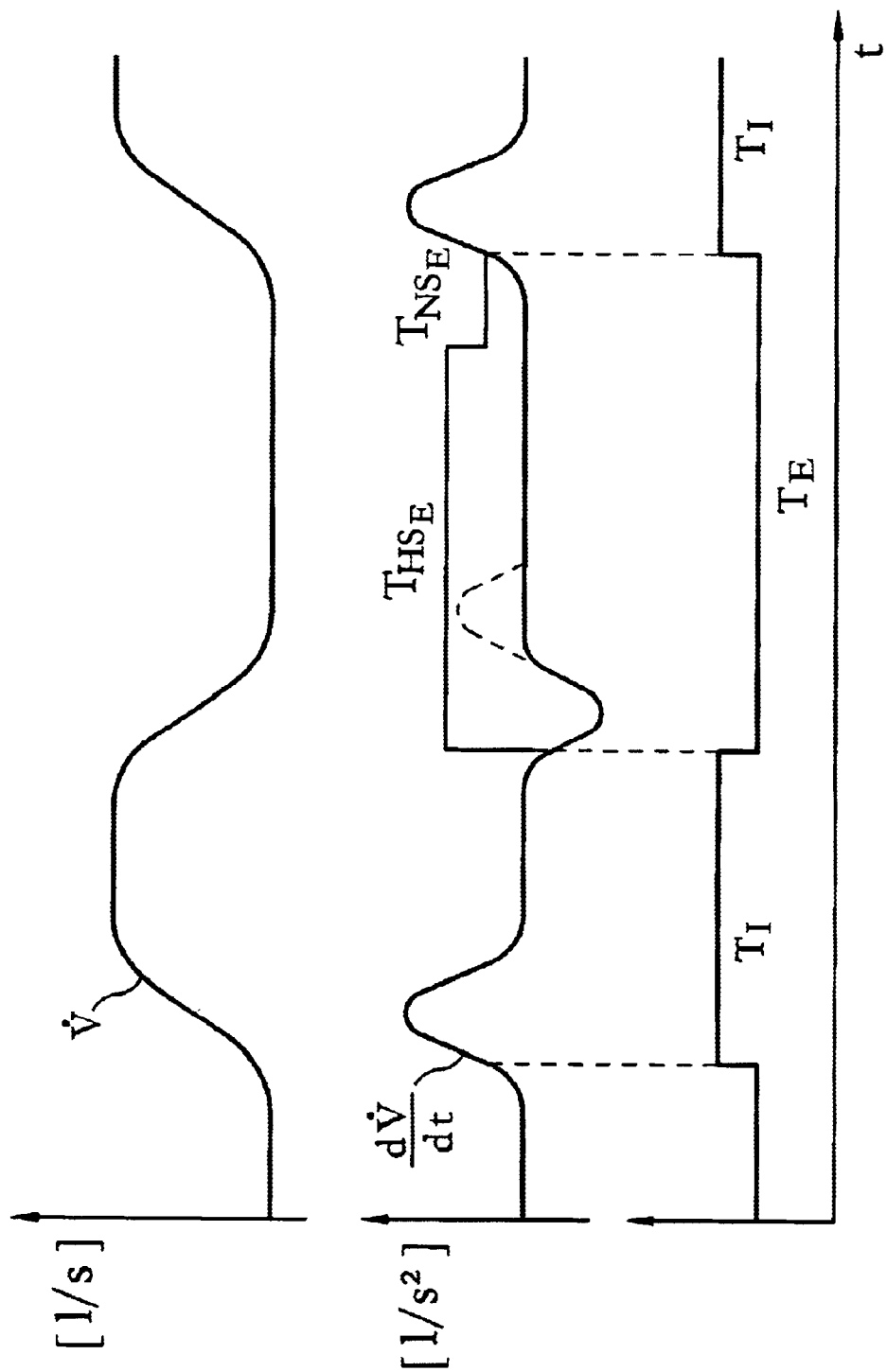

METHOD AND DEVICE FOR SWITCHING THE INSPIRATION OR EXPIRATION PHASE DURING CPAP THERAPY

The present invention relates to a method and a device for switching from the inspiration phase to the expiration phase or vice versa during CPAP (continuous positive airways pressure) therapy in which a positive air pressure is continuously exerted on the airways (CPAP therapy).

The CPAP therapy serves for pneumatically supporting the larynx by continuously supplying a positive air pressure onto the airways. The pressure level is individually adjusted to the patient. The invention is used in a varied CPAP method wherein the expiration takes place at a lower pressure level than the inspiration. This has the advantage that the patient does not have to expire against the high pressure level. It is of great importance for the patient's safety that the adjustment of the different pressure levels during the transition from the inspiration phase to the expiration phase and vice versa takes place with high precision.

In the state of the art, usually the respiratory gas flow from and to the patient is measured and differentiated with respect to time (first derivative) for obtaining a more distinct transition between the inspiration and expiration phases. The derivatives of the flanks of the gas flow curve are compared with threshold values indicating a transition to the respective other breathing phase. However, the patient's respiratory gas flow may comprise deviations; furthermore, influences of the patient's pulse-beat may have an effect on the gas flow. This may result in an overshooting of the first derivative wherein the threshold value for switching to the other breathing phase is achieved prior to the required time so that it is switched to the other pressure level and the patient's safety may be jeopardized. However, it is also possible that the patient's breathing is too shallow so that only a very low rise of the respiratory gas flow curve occurs in the inspiration phase. As a result, the value of the first derivative is so low that the threshold value for the transition to the inspiration phase is not reached.

A method for switching to the inspiration phase or expiration phase in the CPAP therapy is known from EP-A2-0 656 216. In this method, the motor speed and current consumption of a generator for supplying a patient with air is controlled and an operation signal is derived for the purpose of determining the inspiration and expiration phases. A signal representative of the gas flow to the patient is derived from the operation signal. The flow signal d"flow"/dt differentiated with respect to time is compared with a first and a second threshold value and the change in the breathing phase is derived therefrom.

It is the object of the invention to provide an improved method and an improved device for switching to the inspiration or expiration phase in the CPAP therapy, wherein the transition to the inspiration or expiration phase is detected with high precision and the patient's safety is increased.

The object is achieved with the features of the claims.

According to the invention, the solution is based on the following principal concepts.

The first derivative of a respiratory gas flow curve from and to the patient is compared with two subsequent threshold values for the variation of the first derivative. The first threshold value is higher and therefore less sensitive. Deviations which often occur at the beginning of a breathing phase cannot reach said high threshold value and thus trigger any erroneous switching of a pressure level in the CPAP therapy. Subsequent to the high threshold value, a low threshold value which therefore is more sensitive is set for the purpose of determining the transition to the next breathing phase with high precision. The switch to the other breathing phase takes place when the first derivative has reached the second threshold value.

In the case of forced breathing, the high threshold may also be exceeded which is the reason why spontaneous breathing is possible at any time.

If the switching operation to the expiration phase explained above is not triggered, the switching occurs on account of a limiting time switching operation, e.g. at the latest after 3 to 4 s for the inspiration phase.

In a specific embodiment of the present invention, the time dependence of the gas flow in the expiration phase is sampled in a sequence of at least three sampling values in addition to the comparison with the second, low threshold value. If, in such a sequence, the condition is fulfilled that the second and the third sampling values exceed the respective preceding sampling value by a predetermined amount $\Delta$, i.e. the respiratory gas flow rises monotonically, the switch to the inspiration phase occurs at the third sampling value; if this switching does not occur, the switch to the inspiration phase is triggered by the comparison of the first derivative with the low threshold value.

In a preferred embodiment, the first derivative of the respiratory gas flow as well as the respiratory gas flow itself with the corresponding threshold values are monitored and switching to the inspiration phase occurs when one of the two parameters reaches the corresponding threshold value.

A further specific embodiment of the present invention relates to a method for detecting and excluding signals in the respiratory gas flow curve which originate from the pulse-beat (influence of the cardiac activity) of the patient. As a criterion for a pulse-beat signal, the time between its maximum and its minimum and the difference between the maximal and minimal gas flow is used. Upon detection of a pulse-beat signal, the monitoring of the monotonic rise of the respiratory gas flow is stopped or set to a less sensitive value for a short period of time (preferably 1.5 s). Additionally or alternatively, the threshold values for the comparison of the first derivative of the respiratory gas flow can be changed, preferably set to less sensitive values, upon detection of such a pulse-beat signal.

The advantages of the present invention reside both in a lower susceptibility to trouble and in a higher precision during switching to the inspiration or expiration phase in the CPAP therapy.

In the following, the invention is explained in more detail by means of the drawings.

FIG. 1 shows diagrams for illustrating the method according to the invention during switching from the expiration phase to the inspiration phase, FIG. 2 shows diagrams for illustrating the method according to the invention during switching from the inspiration phase to the expiration phase, and FIGS. 3 to 5 show further embodiments of the method according to the invention.

The diagram according to FIG. 1(a) shows the time dependence of the respiratory gas flow curve $\dot{V}$ (e.g. in 1/s). FIG. 1(b) shows the first derivative of the respiratory gas flow curve with respect to time d $\dot{V}$/dt; and FIG. 1(c) shows an enlarged section of the sequence of inspiration phase (inspiration) and expiration phase (expiration) $T_I$ and $T_E$, respectively, which sequence has been derived from the first derivative.

FIG. 1(b) illustrates the transition from the expiration phase to the inspiration phase with respect to two threshold values $HS_E$ and $NS_E$. Following the switch to the expiration phase $T_E$, a high threshold value $HS_E$ is set for triggering the next switch to the inspiration phase. It can be recognized that a possible overshooting (broken line) does not reach the threshold value $HS_E$ and thus cannot trigger any erroneous switching. After a period of time $T_{HS(E)}$ which depends on the duration of the preceding inspiration and is preferably 0.9 times to 1.5 times, more preferably 1.0 times the duration of the preceding inspiration phase $T_I$, a low threshold value $NS_E$ is set. In this range where the transition to the other breathing phase takes place, the low, more sensitive threshold value guarantees an exact determination of the transition time. For the purpose of avoiding an insensitivity of a respective device that lasts too long, the duration of the high threshold $T_{HS(E)}$ in the expiration phase $T_E$ is limited to approximately 3 seconds. Besides, the inspiration can be prevented at the beginning of the expiration phase for a duration of approximately 1 second.

The low threshold value NSE in the expiration phase is only set in the case of a positive value of the gas flow relative to a previous calibration of the system to the gas flow "zero". If this is not the case, the activation of the threshold value NS is delayed by 100 ms each time until a positive value is determined.

Figures 2A, 2B, 2C:
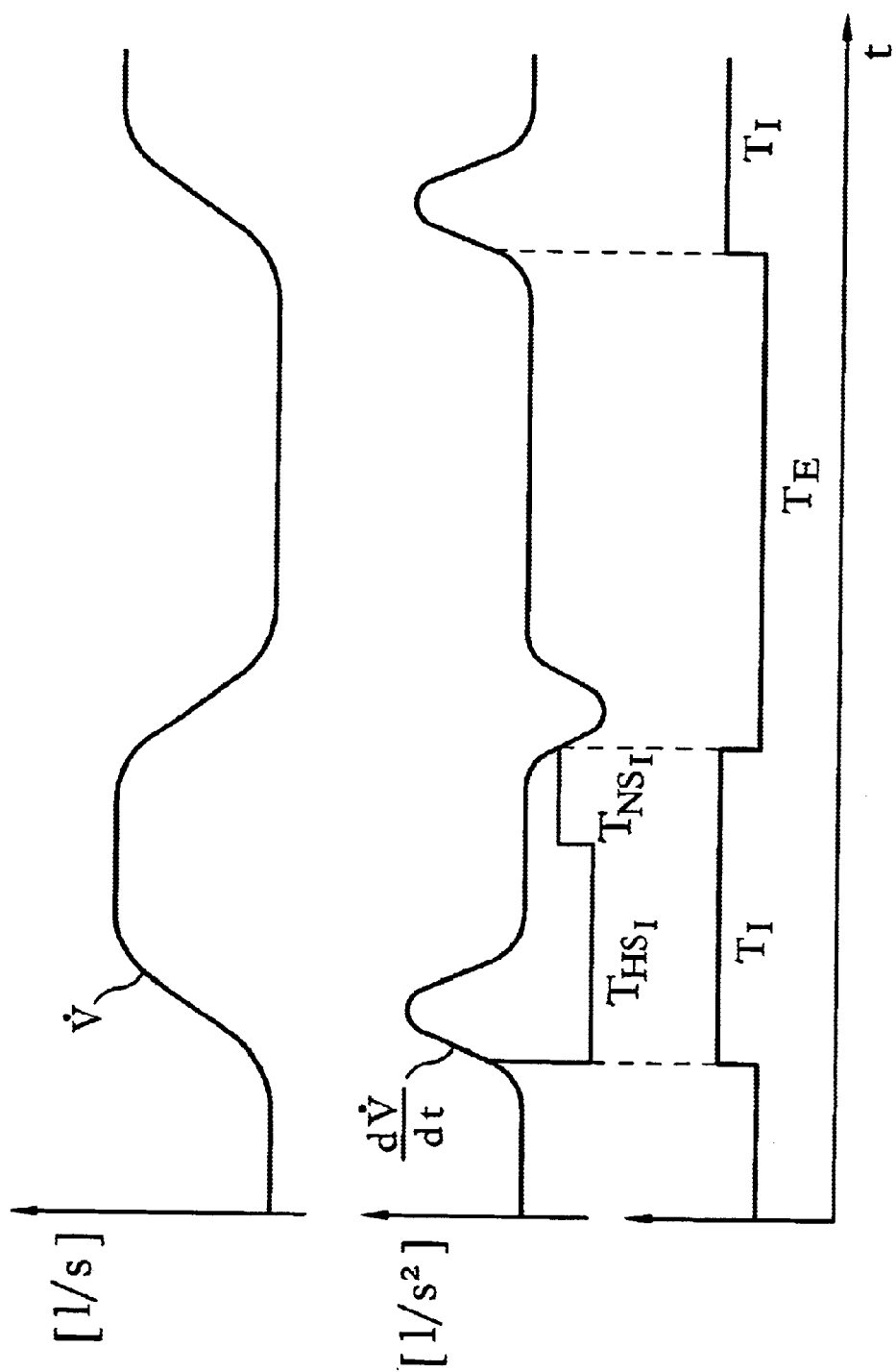
FIG. 2(a) shows the time dependence of the respiratory gas flow curve $\dot{V}$.
FIG. 2(b) shows the first derivative of the respiratory gas flow curve.
FIG. 2(c) shows the sequence of the inspiration and expiration phases which has been derived from the first derivative.

FIG. 2 depicts the transition from the inspiration phase to the expiration phase with respect to the threshold values $HS_I$ and $NS_I$. The high threshold value $HS_I$ means the permission of a deviation from the first derivative towards lower values than at the second threshold value $NS_I$. Hence, after the beginning of the inspiration phase the switching is less sensitive to deviations in the intensity of the first derivative towards lower values which could initiate an unwanted switch to the expiration phase. As in FIG. 1, the smaller deviation of the low threshold value from the first derivative results in an increased sensitivity to a drop of the curve of the first derivative which indicates the transition to the expiration phase.

Figure 3:
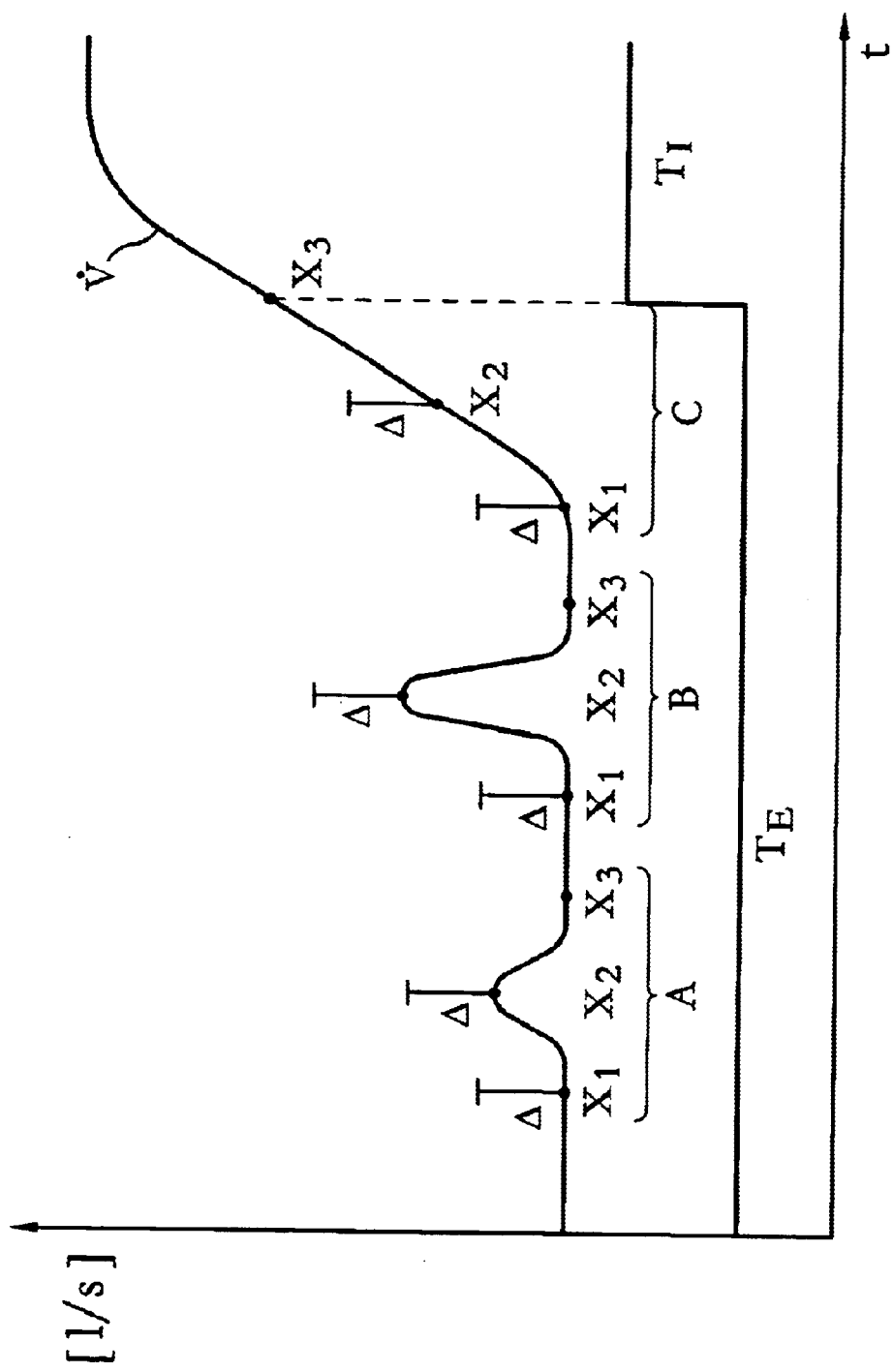

FIG. 3 shows an embodiment according to the invention in which, in addition to the method shown in FIG. 1, the gas flow curve $\dot{V}$ is sampled in a sequence of at least three sampling values $X_1$, $X_2$ and $X_3$ in the expiration phase during the comparison of the first derivative with the second, low threshold value $NS_E$ for the purpose of detecting a monotonic rise of the respiratory gas flow. For the switch to the inspiration phase $T_I$ the condition must be fulfilled that out of three sampling values $X_1$ to $X_3$ the second and third sampling value $X_2$ and $X_3$, respectively, exceed the preceding sampling value $X_1$ or $X_2$, respectively, by a predetermined amount $\Delta$; i.e. the two conditions $X_1+\Delta<X_2$ and $X_2+\Delta<X_3$ must be fulfilled, wherein $\Delta$ is an appropriately predetermined value. It can be deduced from FIG. 3 that only the last sequence C of $X_1$ to $X_3$ values being on the flank of the inspiration gas flow fulfils this condition. In the first sequence A of $X_1$ to $X_3$ values, already the $X_2$ value does not meet the aforementioned criterion, and in the second sequence B of $X_1$ to $X_3$ values, the criterion is fulfilled as regards the value $X_2$ but not as regards $X_3$. It is thus possible to recognize short-term deviations which, for instance, may be due to the patient's pulse-beat and appear relatively large in the first derivative of the gas flow curve $\dot{V}$, so that the switch to the inspiration phase is not triggered by these incorrect signals. The sampling values are to be separated by intervals each of which is longer than the raising time of a pulse wave of the patient; preferably the intervals between the sampling values are 200 to 300 ms each.

By means of a temporal limitation of the inspiration phase of e.g. 3 to 4 s, it is thereafter switched in any case to the expiration phase irrespective of the triggering of the switching by the gas flow signal or by the derivative of the gas flow signal. This method leads to the switching to the inspiration phase also, for instance, in such cases in which the respiration is so shallow that the values of the gas flow curve in the inspiration phase do not reach the low threshold value $NS_I$.

By means of a temporal limitation of the expiration phase of e.g. 1 to 12 s, it is thereafter switched in any case to the inspiration phase irrespective of the triggering of the switching by the gas flow signal or by the derivative of the gas flow signal. This method leads to the switch to the inspiration phase also in such cases in which no spontaneous breathing of the patient is present or recognized so that the values of the gas flow curve in the inspiration phase do not reach the low threshold value $NS_E$.

Figure 4:
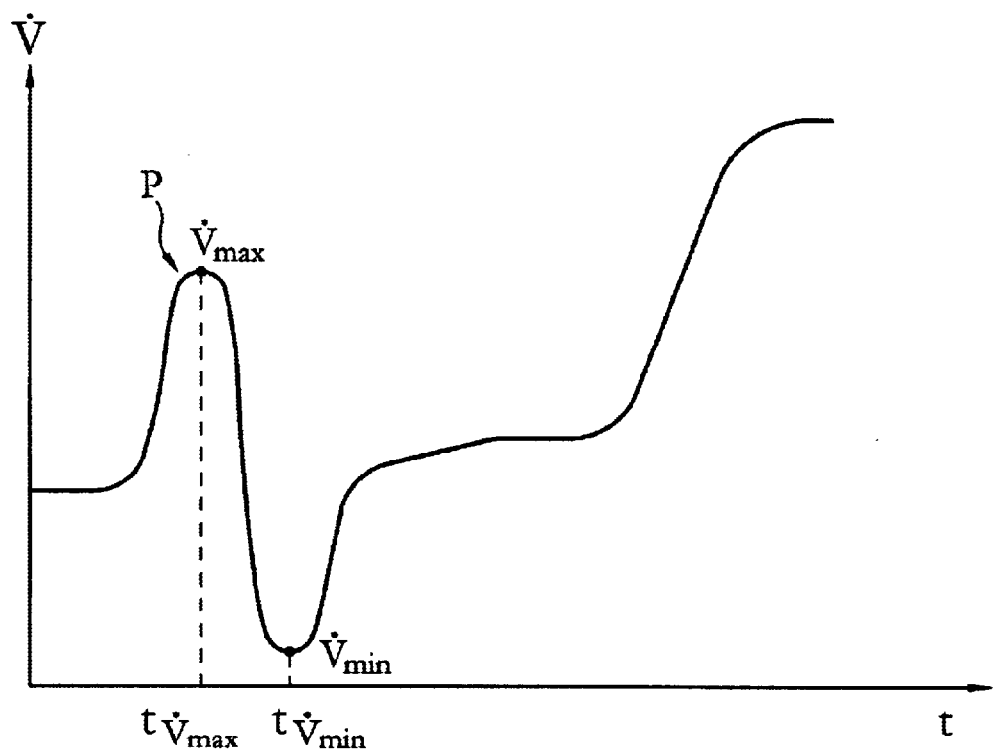

FIG. 4 shows a further embodiment of the invention which allows the detection of unwanted pulse-beat signals originating from the cardiac activity of the patient in the respiratory gas flow curve $\dot{V}(t)$. The pulse-beat has the shape of an oscillation with steep flanks and a corresponding amplitude which is superimposed to the gas flow curve $\dot{V}$. When the steepness of the flank and thus the first derivative of this signal reaches the threshold value for switching to the inspiration phase, an unwanted switching to the inspiration phase may take place prematurely. For the purpose of avoiding such an erroneous switching, a pulse-beat signal P is detected by means of the method according to the invention if the following conditions are fulfilled:

$$\dot{V}_{max} - \dot{V}_{min} \geq \Delta\dot{V}_p \quad (1)$$

$$t_{\dot{V}min} - t_{\dot{V}max} \leq \Delta t_p \quad (2),$$

wherein $\Delta t_p > 0$ $\dot{V}_{max}$=local maximum of the gas flow $\dot{V}_{min}$=local minimum of the gas flow, $t_{\dot{V}max}$=time of the maximal gas flow $t_{\dot{V}min}$=time of the minimal gas flow $\Delta\dot{V}_P$=empirically determined threshold value for changing the gas flow because of a pulse-beat signal $\Delta t_p$=maximal interval between the successive maxima and minima of the pulse-beat signal $\Delta\dot{V}_p$ is preferably 0.5 to 5% of the maximal gas flow in the inspiration phase, $\Delta t_p$ is preferably 400 to 600 ms, particularly preferably 500 ms.

When the conditions (1) and (2) are fulfilled, the monitoring of the monotonic rise of the respiratory gas flow is stopped or set to a less sensitive value for 1 to 3 seconds, preferably for 1.5 seconds, so that an erroneous switching is prevented. Additionally or alternatively, the threshold values for the comparison of the first derivative of the respiratory gas flow can be changed, preferably set to less sensitive values, upon detection of such a pulse-beat signal.

When the method according to FIG. 3 is used in connection with the method according to FIG. 4, the method according to FIG. 3 is interrupted for a predetermined period of time, preferably for 1 to 3 s, particularly preferably for 1.5 s, when the conditions (1) and (2) are fulfilled.

Figure 5:
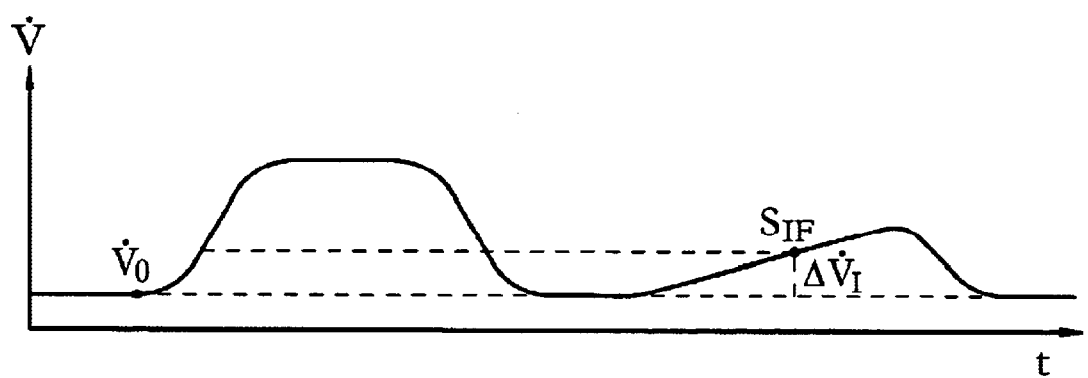

FIG. 5 shows a further embodiment according to the invention wherein a criterion for the switching to the inspiration phase in the case of shallow breathing is shown. The respiratory gas flow curve $\dot{V}(t)$ shows a slow rise of the gas flow in the inspiration phase in the case of shallow breathing. The shallow breathing results in a low first derivative and consequently the threshold value for switching to the inspiration phase is not reached. Therefore, according to the invention, the respiratory gas flow curve $\dot{V}$ is directly used for determining the switching operation and a switching from the expiration to the inspiration phase occurs when the respiratory gas flow $\dot{V}$ has reached a predetermined threshold value $S_{IF}$. In this connection, the following applies:

$$S_{IF} = \dot{V}_0 + \Delta \dot{V}_I \quad (3)$$

$\dot{V}_0$=respiratory gas flow during the last switching to the inspiration phase prior to the beginning of the shallow breathing, in particular during the switching upon evaluation of the first derivative of the respiratory gas flow or monitoring the monotonic rise. In this case, the respiratory gas flow during the last switching upon evaluation of the first derivative is used for determining the respiratory gas flow $\dot{V}_0$.

$\Delta \dot{V}_I$=empirically determined additional respiratory gas flow in the inspiration phase, preferably 1% to 60%, particularly preferably 2 to 5% of the maximal gas flow in the inspiration phase during normal breathing.

$\dot{V}_0$ is measured and stored prior to the last inspiration phase.

The embodiments according to the invention illustrated in FIGS. 4 and 5 can be preferably used in connection with the methods illustrated in FIGS. 1 to 3.

When the method according to FIG. 5 is used in a method with differential evaluation of the respiratory gas flow curve for determining the expiration and inspiration phases, both the first derivative of the respiratory gas flow and the respiratory gas flow itself with corresponding threshold values are monitored and a switching to the inspiration phase occurs when one of the two parameters reaches the corresponding threshold value. Thus, the attainment of the threshold value $S_{IF}$ of the respiratory gas flow curve is the criterion for the switching to the inspiration phase.

The present invention also relates to a device for using the method according to the invention.

What is claimed is:

1. A method for detecting pulse-beat signals (P) in respiratory gas flow in CPAP therapy, wherein a signal of a gas flow curve $\dot{V}(t)$ is detected as a pulse-beat signal (P) when the following conditions are fulfilled:

(a) $\dot{V}_{max} - \dot{V}_{min} \geq \Delta \dot{V}_P$, and
(b) $t_{Vmin} - t_{Vmax} \leq \Delta t_P$, wherein $\Delta t_P > 0$ $\dot{V}_{max}$=local maximum of the respiratory gas flow
$\dot{V}_{min}$=local minimum of the respiratory gas flow
$t_{Vmax}$=time of the maximal respiratory gas flow
$t_{Vmin}$=time of the minimal respiratory gas flow
$\Delta \dot{V}_P$=empirically determined threshold value for a change of the respiratory gas flow because of a pulse-beat signal; and
$\Delta t_P$=maximal interval between successive maxima and minima of the pulse-beat signal, preferably 400 to 600 ms.

2. The method according to claim 1, wherein means are provided for stopping monitoring of a monotonic rise of the respiratory gas flow or setting less sensitive values for a predetermined interval upon detection of the pulse-beat signal (P).

3. The method according to claim 2, wherein the predetermined interval is 1 to 3 s.

4. The method according to claim 3, wherein the predetermined level is 1.5 s.

5. The method according to claim 1 in combination with a device for switching to an inspiration or expiration phase ($T_I$ and $T_E$, respectively) in the CPAP therapy, wherein means are provided for differentiating the respiratory gas flow ($\dot{V}$) from and to a patient with respect to time, wherein after switching to a respective breathing phase, a first derivative ($d\dot{V}/dt$) of the gas flow ($\dot{V}$) is initially compared with a first, high threshold value ($HS_E$, $HS_I$) and then with a second, low threshold value ($NS_E$, $NS_I$) for a variation of the first derivative, wherein a switch to a respective other breathing phase occurs when the first derivative has reached the second threshold value ($NS_E$, $NS_I$).

6. The method according to claim 5, wherein means are provided for sampling a time dependence of the gas flow ($\dot{V}$) in a sequence of at least three sampling values ($X_1$, $X_2$, $X_3$) in the expiration phase, in addition to the comparison of the first derivative with the second, low threshold value ($NS_E$), wherein, if the two conditions $$X_1 + \Delta < X_2 \text{ and } X_2 + \Delta < X_3$$

$\Delta$=predetermined increment are fulfilled, a switch to the inspiration phase occurs at the value $X_3$, unless the switch has already occurred earlier on account of the comparison of the first derivative with the low threshold value ($NS_E$).

7. The method according to claim 6, wherein the sampling values ($X_1$, $X_2$ and $X_3$) are separated by intervals each of which is longer than a raising time of a pulse wave of the patient.

8. The method according to claim 7, wherein the intervals between the sampling values ($X_1$, $X_2$ and $X_3$) are 200 to 300 ms each.

9. The method according to claim 5, wherein a duration ($T_{HS}$) of the comparison of the first derivative with a high threshold value ($HS_E$, $NS_I$) is longer than a duration ($T_{NS}$) of the comparison with the low threshold value ($NS_E$, $NS_I$).

10. The method according to claim 9, wherein the following applies in the expiration phase:

$$T_I \leq T_{HS(E)} < 4S.$$

11. The method according to claim 10, wherein $$T_{HS(E)} \geq (0.9 \text{ to } 1.5) \times T_I.$$

12. The method according to claim 4, wherein $$T_{HS(E)} \geq 1.0 T_I.$$

13. The method according to claim 5, wherein the following applies in the inspiration phase:

$$0.5s < T_{HS(I)} < 3 \text{ s.}$$

14. The method according to claim 5, wherein means are provided for preventing inspiration for 1 second at the beginning of the expiration phase.

15. The method according to claim 5, wherein means are provided for performing a setting of the low threshold value ($NS_E$) in the expiration phase only in the case of a positive value of the gas flow ($\dot{V}$) and otherwise for delaying activation of the threshold value ($NS_E$) by 100 ms each time until a positive value is determined.

16. The method according to claim 5, wherein means are provided for stopping the inspiration phase after 4 s and to switch to the expiration phase unless a switching to the expiration phase has occurred earlier.

17. The method according to claim 5, wherein means are provided for stopping the expiration phase after 1 to 12 s and to switch to the inspiration phase unless a switching to the inspiration phase has occurred earlier.

18. The method according to claim 5, wherein means are provided for performing a switching from the expiration phase to the inspiration phase in the case of shallow breathing when the respiratory gas flow $\dot{V}$ reaches a predetermined threshold value $S_{IF}$.

19. The method according to claim 18, wherein the following applies:

$$S_{IF}=\dot{V}_0+\Delta\dot{V}_I$$

$\dot{V}_0$=respiratory gas flow during a last switching to the inspiration phase prior to the beginning of the shallow breathing during switching upon evaluation of the first derivative of the respiratory gas flow and wherein the respiratory gas flow during the last switching upon evaluation of the first derivative is used for determining the respiratory gas flow $\dot{V}_0$; and $\Delta\dot{V}_I$=empirically determined additional respiratory gas flow in the inspiration phase.

* * * * *